(12) United States Patent
Hammon et al.

(10) Patent No.: US 9,636,651 B2
(45) Date of Patent: May 2, 2017

(54) PLANT AND PROCESS FOR PERFORMANCE OF HETEROGENEOUSLY CATALYZED GAS PHASE REACTIONS

(71) Applicant: BASF SE, Ludwigshafen (DE)

(72) Inventors: Ulrich Hammon, Mannheim (DE); Thomas Walter, Hassloch (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/737,025

(22) Filed: Jun. 11, 2015

(65) Prior Publication Data

US 2015/0360191 A1   Dec. 17, 2015

Related U.S. Application Data

(60) Provisional application No. 62/011,067, filed on Jun. 12, 2014.

(30) Foreign Application Priority Data

Jun. 12, 2014   (DE) .................. 10 2014 108 272

(51) Int. Cl.
C07C 45/00 (2006.01)
C07C 45/27 (2006.01)
(Continued)

(52) U.S. Cl.
CPC ............. B01J 8/0278 (2013.01); B01J 8/065 (2013.01); B01J 8/067 (2013.01); C07C 45/28 (2013.01);
(Continued)

(58) Field of Classification Search
CPC . B01J 8/0278; B01J 8/065; B01J 8/067; B01J 2208/00017; B01J 2208/00893;
(Continued)

(56) References Cited

U.S. PATENT DOCUMENTS 3,904,652 A    9/1975  Frank
4,087,471 A *  5/1978  Bowman ................. C07C 29/04
                                                  568/899
(Continued)

FOREIGN PATENT DOCUMENTS

DE    25 13 405 A1   10/1976
DE    40 23 239 A1    1/1992
(Continued)

OTHER PUBLICATIONS

U.S. Appl. No. 14/661,408, filed Mar. 18, 2015, Hammon, et al.
(Continued)

*Primary Examiner* — Natasha Young
(74) *Attorney, Agent, or Firm* — Oblon, McClelland, Maier & Neustadt, L.L.P.

(57) ABSTRACT

The present invention relates to a plant for performance of heterogeneously catalyzed gas phase reactions. The plant entails a reactor, at least one line leading into the reactor for introduction of reactants into the reactor, at least one first feed for providing at least one first reactant A, which leads into the line, at least one second feed for providing at least one second reactant B, which leads into the line, at least one third feed for providing a cycle gas G, which leads into the line, a temperature control unit which is disposed in the line upstream of the reactor and is for controlling the temperature of the first reactant A and/or second reactant B and/or cycle gas G prior to entry into the reactor and at least one outlet for products, by-products and/or unreacted reactants from the gas phase reaction.

12 Claims, 2 Drawing Sheets

Figure 1:
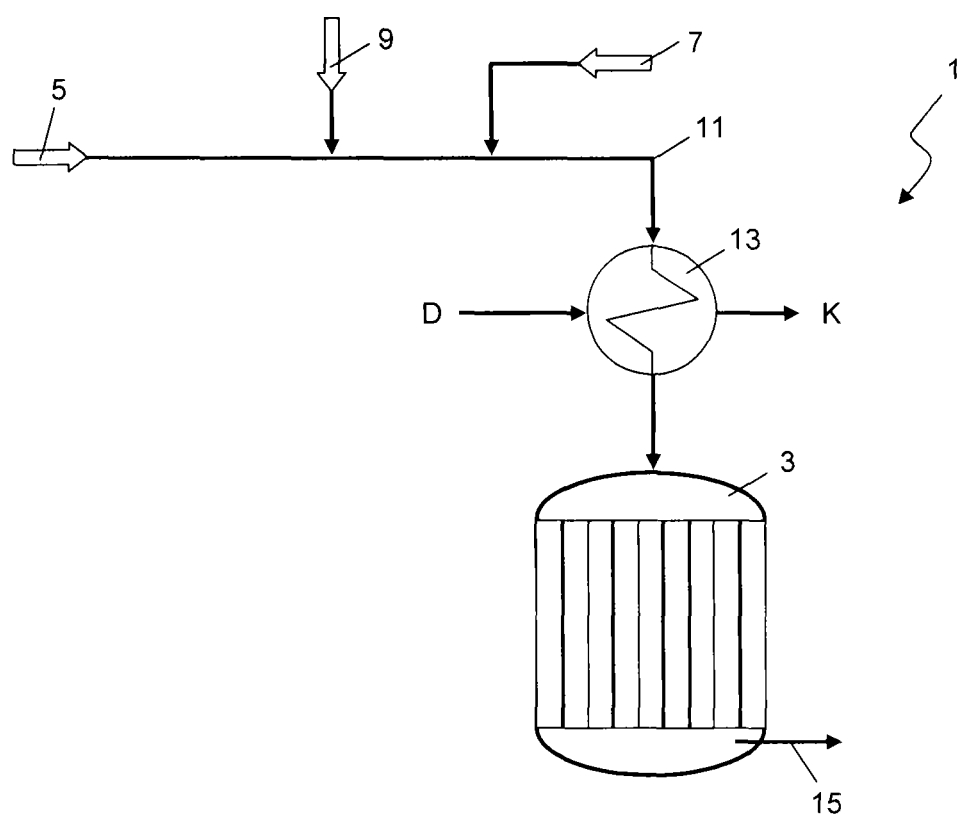

(51) Int. Cl.

| | | |
|---|---|---|
| *C07C 45/28* | (2006.01) | |
| *C07C 45/32* | (2006.01) | |
| *C07C 45/33* | (2006.01) | |
| *C07C 45/34* | (2006.01) | |
| *C07C 45/35* | (2006.01) | |
| *C07C 47/00* | (2006.01) | |
| *C07C 47/20* | (2006.01) | |
| *C07C 47/21* | (2006.01) | |
| *C07C 47/22* | (2006.01) | |
| *C07C 51/00* | (2006.01) | |
| *C07C 51/16* | (2006.01) | |
| *C07C 51/21* | (2006.01) | |
| *C07C 51/25* | (2006.01) | |
| *B01J 8/02* | (2006.01) | |
| *B01J 8/06* | (2006.01) | |
| *B01J 8/00* | (2006.01) | |

(52) U.S. Cl.
CPC .............. *C07C 45/35* (2013.01); *C07C 51/16* (2013.01); *C07C 51/252* (2013.01); *B01J 2208/00017* (2013.01); *B01J 2208/0053* (2013.01); *B01J 2208/00176* (2013.01); *B01J 2208/00893* (2013.01)

(58) Field of Classification Search
CPC ...... B01J 2208/00176; B01J 2208/0053; B01J 8/00; B01J 8/02; B01J 8/06; B01J 2208/00; B01J 2208/00008; B01J 2208/00106; B01J 2208/00168; B01J 2208/0176; B01J 2208/00796; C07C 45/28; C07C 51/252; C07C 45/00; C07C 45/27; C07C 45/32–45/35; C07C 51/00; C07C 51/16; C07C 51/21; C07C 51/25; C07C 47/00; C07C 47/20–47/22
See application file for complete search history.

(56) References Cited

U.S. PATENT DOCUMENTS

| | | | |
|---|---|---|---|
| 5,144,091 | A | 9/1992 | Martan et al. |
| 5,264,625 | A | 11/1993 | Hammon et al. |
| 7,414,149 | B2 * | 8/2008 | DeCourcy .............. B01J 19/002 562/532 |
| 8,299,315 | B2 * | 10/2012 | Brummerstedt Iversen .................... B01J 21/04 44/307 |
| 8,618,336 | B2 | 12/2013 | Macht et al. |
| 2004/0213711 | A1 | 10/2004 | Ha et al. |
| 2005/0020852 | A1 | 1/2005 | Yada et al. |
| 2006/0111575 | A1 | 5/2006 | DeCourcy et al. |
| 2008/0177105 | A1 | 7/2008 | Raichle et al. |
| 2010/0092374 | A1 | 4/2010 | Erkes et al. |
| 2015/0080605 | A1 | 3/2015 | Welker-Nieuwoudt et al. |
| 2015/0133686 | A1 | 5/2015 | Macht et al. |
| 2015/0166455 | A1 | 6/2015 | Hammon et al. |

FOREIGN PATENT DOCUMENTS

| | | |
|---|---|---|
| DE | 41 32 263 A1 | 4/1993 |
| DE | 10 2007 004 961 A1 | 7/2008 |
| DE | 10 2010 048 405 A1 | 5/2011 |
| EP | 1 484 302 A1 | 12/2004 |
| EP | 1 658 893 A1 | 5/2006 |
| WO | WO 2004/007064 A1 | 1/2004 |
| WO | WO 2008/052649 A1 | 5/2008 |

OTHER PUBLICATIONS

U.S. Appl. No. 14/738,033, filed Jun. 12, 2015, Heilek, et al.
U.S. Appl. No. 14/661,462, Mar. 18, 2015, Hammon, et al.
U.S. Appl. No. 14/659,753, Mar. 17, 2015, Hammon, et al.
International Search Report issued on Oct. 9, 2015 in PCT/EP2015/062857 (with English language translation).

* cited by examiner

PLANT AND PROCESS FOR PERFORMANCE OF HETEROGENEOUSLY CATALYZED GAS PHASE REACTIONS

This patent application claims the benefit of U.S. provisional patent application Ser. No. 62/011,067 and DE patent application Serial Number DE 102014108272.9, both filed on Jun. 12, 2014, incorporated in their entirety herein by reference.

The present invention relates to a plant and to a process for performance of heterogeneously catalyzed gas phase reactions.

Plants and processes of this kind are known in principle from the prior art. For instance, DE 41 32 263 A1 describes a process for catalytic gas phase oxidation of acrolein to acrylic acid in a catalyst tube fixed bed reactor at elevated temperature over catalytically active oxides, in which the reaction temperature is subject to a particular temperature profile in two successive reaction zones in flow direction along the catalyst tubes. DE 40 23 239 A1 describes a similar process for catalytic gas phase oxidation of propene or isobutene to acrolein or (meth)acrolein. The aim of these publications is an improvement in the reaction temperature profile with regard to an increased selectivity of the reaction.

A similar aim is pursued by DE 10 2010 048 405 A1, which has for its subject matter a process for long-term operation of a heterogeneously catalyzed partial gas phase oxidation of propene to acrolein. According to this publication, the reaction gas mixture is conducted through a fixed catalyst bed divided into two spatially successive temperature zones A and B. In this process, the fixed catalyst bed is introduced into a reaction chamber, for example into the interior of a (reaction) tube. For a particular length of the total length of the fixed catalyst bed, a homogeneous mixture of shaped catalyst bodies and shaped diluent bodies is provided as a first zone. In a further zone, a less significantly diluted or undiluted fixed catalyst bed is then introduced. Also provided is a pure inert material bed, the length of which, based on the length of the fixed catalyst bed, is 5% to 20%, and which leads toward the fixed catalyst bed in flow direction of the reaction gas mixture. This inert material bed is utilized as the heating zone for the reaction gas mixture.

DE 10 2007 004 961 A1, which relates to a process for producing shaped catalyst bodies, also proposes charging a reaction tube in a first section of about 25% of the total length with an inert preliminary bed and in a second section of about 60% with a catalyst material, leaving a proportion of about 15% of the reaction tube unfilled.

Thus, according to the prior art, 20% or more of the reactor volume is not used for heterogeneously catalyzed gas phase reactions, but for heating of the reaction gas mixture which is supplied at 100° C. to 120° C. This means that (based on the reactor volume) either a lower operating load has to be accepted or that the reactor volume has to be increased once again for a correspondingly higher operating load. Since it is not possible to establish an optimal reaction temperature at the inlet of the reaction tubes by virtue of the cooler reaction gas mixture, moreover, the conversion of the reactants is frequently insufficient.

A further disadvantageous aspect in the prior art which has to be taken into account is the fact that the heating of the reactor or of the reactor volume (including reaction tubes, catalyst bed, inert material bed, heat transfer medium, etc.) to the required reaction temperature of 240° C. to 300° C. entails a very high energy input which is expended only partly for the heating of the reaction gas mixture.

Against this background, it is an object of the present invention to provide a plant and to specify a process which overcome the disadvantages of the prior art and with which it is especially possible to perform heterogeneously catalyzed gas phase reactions in an efficient manner.

This object is achieved firstly by a plant for performance of heterogeneously catalyzed gas phase reactions, comprising
- a reactor (3),
- at least one line (11) leading into the reactor (3) for introduction of reactants into the reactor (3),
- at least one first feed (5) for providing at least one first reactant A, which leads into the line (11),
- at least one second feed (7) for providing at least one second reactant B, which leads into the line (11),
- at least one third feed (9) for providing a cycle gas G, which leads into the line (11),
- a temperature control unit (13) which is disposed in the line (11) upstream of the reactor (3) and is for controlling the temperature of the first reactant A and/or second reactant B and/or cycle gas G prior to entry into the reactor (3) and
- at least one outlet (15) for products, by-products and/or unreacted reactants from the gas phase reaction.

The aforementioned object is also achieved by a process for performing heterogeneously catalyzed gas phase reactions using the plant (1) of the invention, comprising the steps of
a) providing at least one first reactant A in a first feed (5),
b) providing at least one second reactant B in a second feed (7),
c) providing at least one cycle gas G in a third feed (9),
d) mixing the first reactant A, the second reactant B and the cycle gas G to give a reaction mixture R in a line (11),
e) adjusting the temperature of the reaction mixture R in a temperature control unit (13),
f) feeding the temperature-adjusted reaction mixture R to a reactor (3),
g) performing at least one heterogeneously catalyzed gas phase reaction at least between the first reactant A and the second reactant B and
h) removing a mixture of at least one reaction product P and the at least one cycle gas G via at least one outlet (15).

It is a feature of the present invention that the preheating of the reaction mixture R is moved out of the reactor (3) and can thus be undertaken with much lower apparatus complexity. In this way, moreover, essentially the entire reactor volume is available for the gas phase reaction. In addition, the process offers the advantage of introducing energy at a relatively low temperature level and recovering it in the reactor at a much higher level.

If, in the description which follows, process features are among those detailed in connection with the plant (1) of the invention, these preferably relate to the process of the invention. Equally, physical features which are cited in connection with the process of the invention preferably relate to the plant (1) of the invention.

The invention will be described in more detail hereinafter.

The present invention firstly provides a plant (1) for performance of heterogeneously catalyzed gas phase reactions, comprising
- a reactor (3),
- at least one line (11) leading into the reactor (3) for introduction of reactants into the reactor (3),
- at least one first feed (5) for providing at least one first reactant A, which leads into the line (11), at least one second feed (7) for providing at least one second reactant B, which leads into the line (11), at least one third feed (9) for providing a cycle gas G, which leads into the line (11), a temperature control unit (13) which is disposed in the line (11) upstream of the reactor (3) and is for controlling the temperature of the first reactant A and/or second reactant B and/or cycle gas G prior to entry into the reactor (3) and at least one outlet (15) for products, by-products and/or unreacted reactants from the gas phase reaction.

The plant of the invention has the advantage that the temperature control unit (13), the device for preheating the reaction mixture, has been moved out of the reactor (3) and can be operated with a different heat transfer medium than that needed for the heating of the reactor (3). It is thus possible to introduce energy streams that have to be removed in the process back into the process at a comparatively low temperature level and to recover them as high-pressure steam at a higher energy level.

The first reactant A may, in accordance with the invention, be a liquid or gaseous compound or a mixture of two or more of these compounds. Very specific examples are liquid propylene, propane, acrolein and (meth)acrolein, butane, n-butene or isobutene.

The second reactant B may, likewise in accordance with the invention, be a liquid or gaseous compound or a mixture of two or more of these compounds, but preference is given in accordance with the invention to oxygenous gases, especially air.

The heterogeneously catalyzed gas phase reactions for which the plant (1) of the invention has been designed are especially heterogeneously catalyzed, non-partial or partial gas phase oxidations of propene, propane or isobutene to acrolein or (meth)acrolein, of n-butene to maleic acid and of acrolein or (meth)acrolein to acrylic acid or (meth)acrylic acid.

In the context of the present invention, the cycle gas G is understood to mean a gas which serves to dilute the reactants A and B and to take up heat of reaction, and which has substantially inert behavior in the gas phase reaction. The cycle gas G may comprise nitrogen, water vapor, carbon oxides and mixtures thereof.

In the above definition of the plant (1) of the invention, only the plant components essential to the invention have been detailed. Plant components that are obvious to the person skilled in the art, for example a heating and circulation apparatus for a heat transfer medium for the reactor (3) or necessary inlets and outlets, have not been described explicitly but are not excluded from the scope of the definition.

In a preferred embodiment, the reactor (3) is a shell and tube reactor having reaction tubes filled essentially completely with a catalytically active material. Since the plant (1) of the invention comprises a temperature control unit (13), there is no need to provide a zone for preheating of the reactants A, B and/or cycle gas G (optionally with an inert bed) in the reactor (3), and so essentially the full volume of the reaction tubes of a shell and tube reactor is available for the gas phase reaction. Given the same reactor volume, it is thus possible to achieve a higher operating load.

Generic plants for performance of heterogeneously catalyzed gas phase reactions have to be run down and shut down for maintenance operations at regular intervals, for example in order to exchange the catalyst charge. For this purpose, a cooled gas, for example the cycle gas G or air, is generally used. According to the prior art, this gas is cooled down by means of a separate cooler (heat exchanger) before being fed to the reactor of the plant, in order to cool the reactor itself from the inside. Since the reactor, because of its stable metallic design and the large amounts of heat transfer medium, has a high heat capacity, additional capital costs are necessary for the pipework of lines of corresponding dimensions, as is a high energy input for the cooling.

In order to reduce the capital costs and the energy input, in a development of the invention, the temperature control unit (13) is configured as a heat exchanger operable as a preheater or as a cooler. In regular operation, i.e. in the course of performance of heterogeneously catalyzed gas phase reactions, the temperature control unit (13), i.e. the heat exchanger, serves to preheat the gas mixture which is fed to the reactor (3). In maintenance operation, the same temperature control unit (13) is operated as a heat exchanger in the opposite direction, meaning that it now serves to cool the gas fed to the reactor (3).

Even though the temperature control unit (13) of the invention, in this embodiment, has to have a more complex configuration than a straight preheater or a straight cooler, the apparatus complexity for the plant of the invention and hence the capital costs can be distinctly lowered.

The present invention further provides a process for performing heterogeneously catalyzed gas phase reactions using the plant (1) of the invention, comprising the steps of
a) providing at least one first reactant A in a first feed (5),
b) providing at least one second reactant B in a second feed (7),
c) providing at least one cycle gas G in a third feed (9),
d) mixing the first reactant A, the second reactant B and the cycle gas G to give a reaction mixture R in a line (11),
e) adjusting the temperature of the reaction mixture R in a temperature control unit 13),
f) feeding the temperature-adjusted reaction mixture R to a reactor (3),
g) performing at least one heterogeneously catalyzed gas phase reaction at least between the first reactant A and the second reactant B and
h) removing a mixture of at least one reaction product P and the at least one cycle gas G via at least one outlet (15).

The process of the invention has essentially the same advantages as the above-described system (1). More particularly, it is possible by means of the temperature control unit (13) of the invention to move the preheating of the reaction mixture R out of the reactor (3) and to undertake it with much lower energy expenditure than is possible according to the prior art.

In addition, according to the invention, essentially the whole reactor volume is available for the gas phase reaction, and so a higher operating load can be achieved with the same reactor volume.

In a development of the process of the invention, the temperature control unit (13) is operated in step d) as a heat exchanger for preheating of the reaction mixture R. In this way, it is possible to establish a more homogeneous temperature distribution which is more optimal for the gas phase reaction in the reactor (3), since the reactor is not supplied with a cooler reaction mixture R. Moreover, the reaction mixture R arrives at a catalyst charge at a higher temperature, which leads to better product yields.

It is additionally preferable for an optimal conversion of the reactants A and B when the reaction mixture R is preheated in the temperature control unit (13) in step d) to a temperature of 60% to 100% of the reaction temperature in the reactor (3).

It has been found to be advantageous for the energy balance of the process of the invention when the temperature control unit (13), i.e. the heat exchanger, is supplied with hot process steam D as heat transfer medium. At major chemical industry sites, hot process steam D is generally obtained as comparatively low-value energy on a large scale and is available for various uses. By using this comparatively low-value energy, especially process steam D at 10 bar to 25 bar, in the temperature control unit (13) of the invention for preheating of the reaction mixture R, it is possible to save higher-value energy, i.e. high-pressure steam at at least 35 bar, which has to be used for heating of the reactor (3), for example, compared to the prior art.

As described above, generic plants for performance of heterogeneously catalyzed gas phase reactions have to be run down and shut down at regular intervals for maintenance operations. This necessity is taken into account by a further embodiment of the process, by executing the following steps at time intervals:

i) stopping steps a) and b),
ii) conducting step c),
iii) stopping step d),
iv) adjusting the temperature of the cycle gas G in the temperature control unit (13),
v) feeding the temperature-adjusted cycle gas G to the reactor (3),
vi) stopping step g),
vii) removing the cycle gas G via the outlet (15).

In this way, in a simple but efficient manner, the actual heterogeneously catalyzed gas phase reaction is stopped and the process is put into a maintenance or servicing mode.

In a development of this embodiment, the temperature control unit (13) is operated in step d) as a heat exchanger for cooling of the cycle gas G. By this measure, it is possible in an advantageous manner to reduce the capital costs for a plant (1) of the invention and the energy input for the process of the invention. Compared to regular operation for performance of the heterogeneously catalyzed gas phase reactions, the mode of operation of the temperature control unit (13), i.e. the heat exchanger, is reversed here, and it is used for cooling of the gas supplied to the reactor (3).

For the energy efficiency, it has been found to be advisable for the temperature control unit (13) to be supplied with cold condensate K as heat transfer medium. Cold condensate K is generally obtained in comparatively large volumes in major chemical industry sites (similarly to hot process steam D). After being used as cooling heat transfer medium, the condensate K is additionally available as hot condensate HK, which has a sufficient energy content for the further use. It is thus possible to further improve the local energy balance of the chemical industry site.

Figure 2:
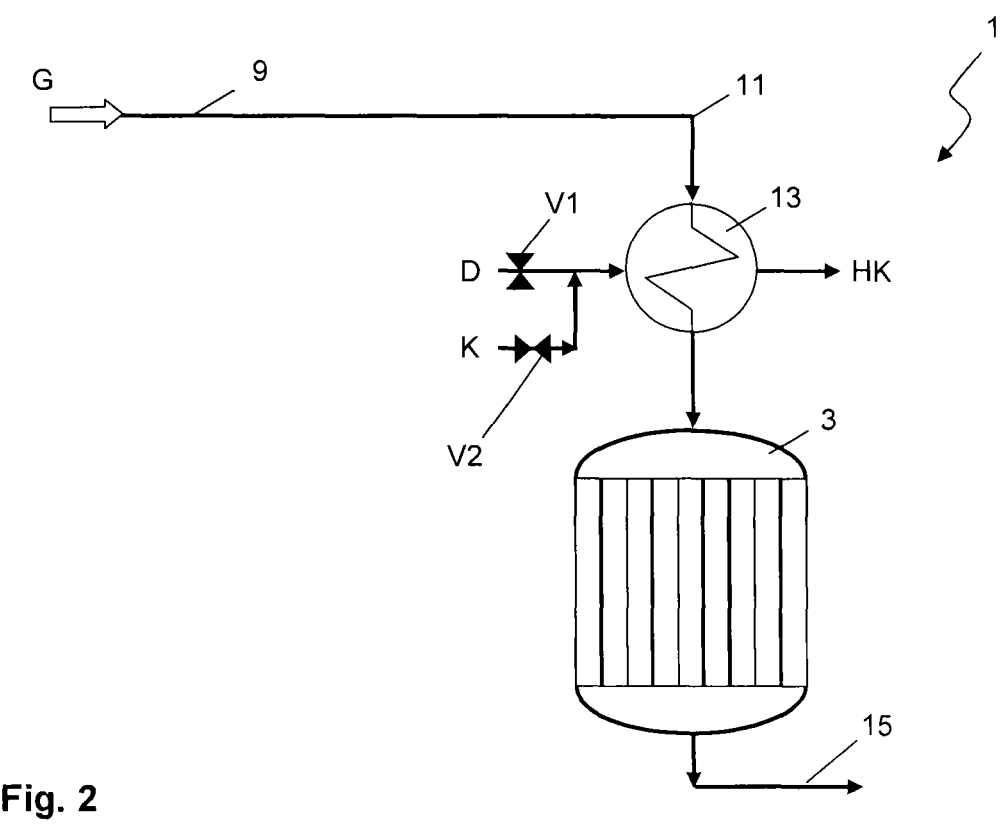

Further aims, features, advantages and possible uses are apparent from the description of working examples of the present invention that follows, with reference to the figures. All the features described and/or shown pictorially, alone or in any combination, form the subject matter of the present invention, even with no regard to the way in which they are recited in the claims or the dependency references thereof. The figures show:

FIG. 1 a schematic diagram of the plant (1) in a first embodiment of the invention and FIG. 2 a schematic diagram of the plant (1) in a second embodiment of the invention.

FIG. 1 shows a first embodiment of the present invention. From a reservoir vessel which is not shown in detail, a liquid or gaseous reactant A is provided via the first feed 5. This reactant A is then mixed with a preheated cycle gas G at the third feed 9, such that the reactant A, if it was in liquid form, is essentially fully evaporated. The second reactant B is fed in via the second feed 7 and mixed with the mixture of reactant A and cycle gas G, so as to obtain the reaction mixture R.

The reaction mixture R is introduced into the temperature control unit 13 via a line 11, where it is preheated to a temperature of 200° C. with process steam D in this embodiment. The reaction mixture R thus preheated is fed to the reactor 3, in the present embodiment a shell and tube reactor with a fixed bed catalyst charge.

Since the reaction mixture R has already been preheated to a sufficient temperature for the heterogeneously catalyzed gas phase reaction, the reaction tubes of the shell and tube reactor 3 are filled essentially completely with catalytically active material, and so the conversion of the reactants A and B is already taking place at the start of the reaction tubes. The product(s), by-products and/or unreacted reactants A and B are removed from the reactor 3 via an outlet 15.

The diagram in FIG. 1 omits the equipment known in principle from the prior art for the further workup of the product(s) and the by-products, for example absorption columns, desorption columns, distillation columns, crystallizers or the like.

While FIG. 1 shows the plant 1 of the invention in reaction mode, FIG. 2 shows a further embodiment for the maintenance and servicing of the plant. The first feed 5 and the second feed 7 for the reactants A and B are not shown, since the reactants are not provided in maintenance mode. The cycle gas G is provided by the third feed 9 and fed to the temperature control unit 13 via the line 11. The temperature control unit 13, which takes the form of a heat exchanger, in this embodiment is no longer operated with process steam D for preheating of the reaction mixture R. The feed of process steam D is stopped by closing the valve $V_1$, and cold or precooled condensate K is instead fed in, prior to the opening of the valve $V_2$, in order to cool down the cycle gas G in the temperature control unit 13.

The cycle gas G which has been cooled down in this way is fed to the reactor 3 in order to cool said reactor in turn from the inside. The heat exchange heats the cooled condensate K to give hot condensate HK, which has other viable further uses.

The cycle gas G heated in the reactor is withdrawn via the outlet 15 and provided at the third feed 9 essentially via a circulation system which is not shown, in order to be fed back again to the temperature control unit 13 which acts as a cooler.

The diagram in FIG. 2 also does not show some plant components, for example the circulation system and possible collection and storage vessels for the heat transfer medium, which is flushed around the reaction tubes of the shell and tube reactor in reaction mode. This heat transfer medium is of course likewise discharged from the reactor 3 in order to be able to cool it down sufficient.

The invention claimed is:
1. A plant comprising
   a reactor,
   at least one line leading into the reactor, configured for introduction of reactants into the reactor,
   at least one first feed, configured for providing at least one first reactant A, which leads into the line,
   at least one second feed, configured for providing at least one second reactant B, which leads into the line,
   at least one third feed, configured for providing a cycle gas G, which leads into the line, a temperature control unit which is disposed in the line upstream of the reactor and is configured for controlling a temperature of the first reactant A or second reactant B or cycle gas G prior to entry into the reactor, wherein the temperature control unit is a heat exchanger operable as a preheater or as a cooler, at least one outlet, configured for products, by-products or unreacted reactants from a gas phase reaction, a fourth feed for feeding of process steam D to the temperature control unit, wherein the fourth feed comprises a valve $V_1$, a fifth feed for feeding of cold condensate K to the temperature control unit, wherein the fifth feed comprises a valve $V_2$, and a second outlet for condensate K or hot condensate HK leading out of the temperature control unit.

2. The plant of claim 1, wherein the reactor is a shell and tube reactor having reaction tubes filled essentially completely with a catalytically active material.

3. The plant of claim 1, wherein the temperature control unit is a heat exchanger operable as a preheater.

4. The plant of claim 1, wherein the temperature control unit is a heat exchanger operable as a cooler.

5. The plant according to claim 1, wherein in the course of performance of heterogeneously catalyzed gas phase reactions, the temperature control unit serves to preheat the gas mixture which is fed to the reactor, and in maintenance operation the same temperature control unit is operated as a heat exchanger in the opposite direction and serves to cool the gas fed to the reactor.

6. A process for performing a heterogeneously catalyzed gas phase reaction in the plant of claim 1, the process comprising:

mixing the first reactant A, the second reactant B and the cycle gas G to give a reaction mixture R in the line, b) adjusting a temperature of the reaction mixture R in the temperature control unit, to obtain a temperature-adjusted reaction mixture R, c) feeding the temperature-adjusted reaction mixture R to the reactor, d) performing at least one heterogeneously catalyzed gas phase reaction at least between the first reactant A and the second reactant B, to obtain at least one reaction product P, and e) removing a mixture of the at least one reaction product P and the at least one cycle gas G via the outlet.

7. The process of claim 6, wherein the temperature control unit operated in a) as a heat exchanger that preheats the reaction mixture R.

8. The process of claim 7, wherein the temperature control unit is fed with hot process steam D as a heat transfer medium.

9. The process of claim 6, wherein the reaction mixture R is preheated in the temperature control unit in a) to a temperature of 60% to 100% of the reaction temperature in the reactor.

10. The process of claim 6, comprising performing i)-vii) at time intervals:

i) stopping a feed of the first reactant A and a feed of the second reactant B to the line, ii) feeding the cycle gas G to the line, iii) stopping the mixing a), iv) adjusting the temperature of the cycle gas G in the temperature control unit, v) feeding the temperature-adjusted cycle gas G to the reactor, vi) stopping the at least one heterogeneously catalyzed gas phase reaction d), and vii) removing the cycle gas G via the outlet.

11. The process of claim 10, wherein the temperature control unit is operated in a) as a heat exchanger that cools the cycle gas G.

12. The process of claim 10, wherein the temperature control unit is supplied with cold condensate K as a heat transfer medium.

* * * * *